US009993402B2

(12) United States Patent
Gershon et al.

(10) Patent No.: US 9,993,402 B2
(45) Date of Patent: Jun. 12, 2018

(54) SUNSCREEN ADDITIVES FOR ENHANCING VITAMIN D PRODUCTION

(71) Applicant: International Business Machines Corporation, Armonk, NY (US)

(72) Inventors: Talia S. Gershon, White Plains, NY (US); Ning Li, Yorktown Heights, NY (US); Devendra Sadana, Yorktown Heights, NY (US); Teodor K. Todorov, Yorktown Heights, NY (US)

(73) Assignee: International Business Machines Corporation, Armonk, NY (US)

( * ) Notice: Subject to any disclaimer, the term of this patent is extended or adjusted under 35 U.S.C. 154(b) by 87 days.

(21) Appl. No.: 15/082,624

(22) Filed: Mar. 28, 2016

(65) Prior Publication Data

US 2017/0065498 A1 Mar. 9, 2017

Related U.S. Application Data

(60) Provisional application No. 62/213,679, filed on Sep. 3, 2015.

(51) Int. Cl.
*A61K 8/00* (2006.01)
*A61K 8/19* (2006.01)
*A61K 8/27* (2006.01)
*A61K 8/26* (2006.01)
*A61K 8/24* (2006.01)
*A61K 8/02* (2006.01)
*A61Q 17/04* (2006.01)
*C09K 11/64* (2006.01)
*C09K 11/77* (2006.01)

(52) U.S. Cl.
CPC .............. *A61K 8/19* (2013.01); *A61K 8/0241* (2013.01); *A61K 8/24* (2013.01); *A61K 8/26* (2013.01); *A61K 8/27* (2013.01); *A61Q 17/04* (2013.01); *C09K 11/641* (2013.01); *C09K 11/7712* (2013.01); *C09K 11/7721* (2013.01); *C09K 11/7734* (2013.01); *C09K 11/7749* (2013.01); *C09K 11/7764* (2013.01); *C09K 11/7777* (2013.01)

(58) Field of Classification Search
None
See application file for complete search history.

(56) References Cited

U.S. PATENT DOCUMENTS

| | | | |
|---|---|---|---|
| 3,761,261 A | 9/1973 | Ono et al. | |
| 3,863,007 A | 1/1975 | Warner, Jr. | |
| 4,549,195 A | 10/1985 | Bluzer | |
| 5,011,782 A | 4/1991 | Lamb | |
| 5,147,125 A | 9/1992 | Austin | |
| 5,223,250 A | 6/1993 | Mitchell | |
| 5,441,726 A | 8/1995 | Mitchnick | |
| 5,534,056 A | 7/1996 | Kuehnle | |
| 6,419,909 B1 | 7/2002 | Lorant | |
| 7,241,399 B2 * | 7/2007 | Haubold | B82Y 20/00 106/401 |
| 9,056,063 B2 | 6/2015 | Hanson | |
| 9,144,535 B1 | 9/2015 | Daly et al. | |
| 9,144,536 B1 | 9/2015 | Daly et al. | |
| 2002/0122832 A1 | 9/2002 | Hanke | |
| 2003/0102099 A1 | 6/2003 | Yadav | |
| 2004/0209081 A1 | 10/2004 | Hagihara | |
| 2005/0008861 A1 | 1/2005 | Yadav et al. | |
| 2005/0048010 A1 | 3/2005 | Kliss | |
| 2005/0208005 A1 | 9/2005 | Giroud | |
| 2005/0227063 A1 | 10/2005 | Lawandy | |
| 2005/0265935 A1 | 12/2005 | Hollingsworth | |
| 2006/0228310 A1 | 10/2006 | Lyth | |
| 2006/0270053 A1 | 11/2006 | Tilak | |

(Continued)

FOREIGN PATENT DOCUMENTS

CN 103071535 A 5/2013
EP 1889810 A1 2/2008

(Continued)

OTHER PUBLICATIONS

Ultraviolet Radiation and the INTERSUN Programme [online]. WHO, Nov. 2003 [retrieved on Jun. 8, 2017]. Retrieved from the internet <http://www.who.int/uv/uv_and_health/en/>.
Thokozane Moses Sithole, Synthesis and characterization of MBxOy:Eu (M=Ca, Sr, Ba) phosphors and TiO2 semiconductor for application in luminescence and energy materials, University of the Free State, Nov. 2014.
Sardar et al., Optical-absorption intensities and intermanifold emission cross sections of trivalent erbium ions in calcium fluorophosphate, Journal of Applied Physics, Sep. 2005.
Lu et al., 2008—White Up-Conversion Luminescence in Rare-Earth-Ion-Doped YAlO3 Nanocrystals, J. Phys. Chem. C 2008, 112, 15071-15074.

(Continued)

*Primary Examiner* — Nannette Holloman
(74) *Attorney, Agent, or Firm* — Ryan, Mason & Lewis, LLP

(57) ABSTRACT

Sunscreen additives for enhancing vitamin D production are provided herein. A method includes selecting phosphor materials to incorporate into zinc oxide particles, wherein the phosphor materials are capable of carrying out an up-conversion process whereby two or more photons absorbed by the zinc oxide particles and/or the phosphor materials within a first wavelength range are emitted as at least one photon within a second wavelength range. The method also includes incorporating the selected phosphor materials into the zinc oxide particles. A composition includes zinc oxide particles suspended within a medium of a sunscreen composition, and phosphor materials incorporated into the zinc oxide particles, wherein the phosphor materials are capable of carrying out an up-conversion process whereby two or more photons absorbed by the zinc oxide particles and/or the phosphor materials within a first wavelength range are emitted as at least one photon within a second wavelength range.

19 Claims, 1 Drawing Sheet

(56) References Cited

U.S. PATENT DOCUMENTS

| | | |
|---|---|---|
| 2007/0280895 A1 | 12/2007 | Weimer |
| 2008/0149850 A1 | 6/2008 | Tardif et al. |
| 2008/0220026 A1 | 9/2008 | Maltra |
| 2009/0022765 A1 | 1/2009 | Chung et al. |
| 2009/0104130 A1* | 4/2009 | Bernstein ............... A61K 8/19 424/59 |
| 2009/0258072 A1 | 10/2009 | Schlossman |
| 2009/0258230 A1 | 10/2009 | Schlossman |
| 2010/0008872 A1 | 1/2010 | Katusic |
| 2010/0055138 A1 | 3/2010 | Margulies |
| 2011/0268678 A1 | 11/2011 | Armstrong |
| 2013/0216834 A1 | 8/2013 | Hashimoto |
| 2014/0142213 A1 | 5/2014 | Weiss |
| 2015/0283059 A1 | 10/2015 | Nagare |
| 2016/0082513 A1 | 3/2016 | Niedermeyer |

FOREIGN PATENT DOCUMENTS

| | | |
|---|---|---|
| JP | 09059591 A | 3/1997 |
| JP | 2008024677 A | 2/2008 |
| JP | 2011102291 A | 5/2011 |
| WO | 2005023535 A2 | 3/2005 |
| WO | 2008017176 A2 | 2/2008 |
| WO | 2008079758 A1 | 7/2008 |
| WO | 2011004133 A2 | 1/2011 |
| WO | 2012046204 A1 | 4/2012 |
| WO | 2013040149 | 3/2013 |
| WO | 2013094639 A1 | 6/2013 |
| WO | 2014049139 A1 | 4/2014 |
| WO | 2014077189 | 5/2014 |
| WO | 2016020168 A1 | 2/2016 |

OTHER PUBLICATIONS

Refractive index of ZnO (Zinc oxide)—Bond-o, http://refractiveindex.info/?shelf=main&book=ZnO&page=Bond-o, Mar. 25, 2016.

Refractive index of SiO2 (Silicon dioxide, Silica, Quartz)—Malitson, http://refractiveindex.info/?shelf=main&book=SiO2&page=Malitson, Mar. 25, 2016.

Schubert et al., Design of multilayer antireflection coatings made from co-sputtered and low-refractive-index materials by genetic algorithm. Optics Express vol. 16, No. 8, 2008.

Law et al., ZnO—Al2O3 and ZnO—TiO2 Core-Shell Nanowire Dye-Sensitized Solar Cells. J. Phys. Chem. B 2006, 110, 22652-22663.

Pu et al., Core/shell structured ZnO/SiO2 nanoparticles: Preparation, characterization and photocatalytic property. Applied Surface Science 257 (2010) 393-397.

Mantz et al., Progress in Organic Coatings 47 (2003) 432-442, "A multiple-scattering model analysis of zinc oxide pigment for spacecraft thermal control coatings."

Song et al., Toxicology Letters 199 (2010) 389-397, "Role of the dissolved zinc io and reactive oxygen species in cytotoxicity of ZnO nanoparticles."

Bohren et al., "Absorption and Scattering of Light by Small Particles", Wiley-VCH, © 2004, Weinheim.

Bae et al., J. Phys. Chem. B 2005, 109, 2526-2531, "Comparative Structure and Optical Properties of Ga-, In-, and Sn-Doped ZnO Nanowires Synthesized by thermal evaporation."

NanoComposix, Silver Nanoparticles: Optical Properties, http://nanocomposix.com/pages/silver-nanoparticles-optical-properties, Apr. 20, 2016.

Awazu et al., 2007—A Plasmonic Photocatalyst Consisting of Silver Nanoparticles Embedded in Titanium Dioxide, J. Am. Chem. Soc. 2008, 130, 1676-1680.

Sherry et al., Localized Surface Plasmon Resonance Spectroscopy of Single Silver Nanocubes, Nano Lett., vol. 5, No. 10, 2005.

Aguirre et al., Ag@ZnO Core_Shell Nanoparticles Formed by the Timely Reduction of Ag+ Ions and Zinc Acetate Hydrolysis in N,N-Dimethylformamide: Mechanism of Growth and Photocatalytic Properties, J. Phys. Chem. C 2011, 115, 24967-24974.

Haynes et al., Nanosphere Lithography: Tunable Localized Surface Plasmon Resonance Spectra of Silver Nanoparticles, J. Phys. Chem. B 2000, 104, 10549-10556.

U. Nobbmann, "FAQ: How important are refractive index & adsorption for nanoparticles?" http://www.materials-talks.com/blog/2014/08/05/faq-how-important-are-refractive-index-absorption-for-nanoparticles/ Materials Talks, Aug. 5, 2014, p. 1-2.

Tsuzuki et al., Nanoparticle Coatings for UV Protective Textiles, RJTA vol. 14 No. 2 2010.

Li et al., Transparent and Light-Emitting Epoxy Super-Nanocomposites Containing ZnO-QDs/SiO2 Nanocomposite Particles as Encapsulating Materials for Solid-State Lighting, J. Phys. Chem. C 2008, 112, 18616-18622.

Li et al., 2011—Sol-gel preparation and characterization of nanoporous ZnO_SiO2 coatings with broadband antireflection properties, Applied Surface Science 257 (2011) 9752-9756.

Messaoudi et al., "Synthesis and characterization of ZnO/Cu2O core-shell nanowires grown by two-step electrodeposition method." Applied Surface Science 343 (2015) 148-152.

Luo et al., Facile synthesis of composition-tuned ZnO/ZnxCd1-xSe nanowires for photovoltaic applications, Nanoscale Research Letters (2015) 10:181.

List of IBM Patents or Applications Treated as Related.

Faure, B. et al. Dispersion and Surface Functionalization of Oxide Nanoparticles for Transparent Photocatalytic and UV-protecting Coatings and Sunscreens, Sci Technol. Adv. Mater. 14 2013, 023001.

Naylor et al. "Sunscreens," accessed 2017, http://telemedicine.org/sundam/sundam2.4.2.html.

Smijs et al. Titanium Dioxide and Zinc Oxide Nanoparticles in Sunscreens: Focus on Their Safety and Effectiveness, Nanotechnology, Science and Applications 4:95-112, Oct. 2011.

Wikipedia, List of Refractive Indices, last modified Feb. 15, 2017; https://en.wikipedia.org/wiki/List_of_refractive_indices.

Tariq Jan, et al. Sn Doping Induced Enhancement in the Activity of ZnO Nanostructures Against Antibiotic Resistant S. aureus Bacteria; Int J. Nanomedicine, vol. 8, pp. 3679-3687; Published online Sep. 30, 2013.

Bhatti et al. Optical Properties of Chromium & Cobalt Doped Zinc Oxide Powder Prepared by Sol-Gel Combustion Method, with the Assistance of Microwave Radiations; International Journal of Advanced Tech. in Engineering and Science; vol. 3, Issue 10; pp. 80-85; published Oct. 2015.

Famity Health Team, "Best Ways to Protect Your Hair From Sun Damage," Cleveland Clinic, health essentials, <https://health.clevelandclinic.org/2014/08/best-ways-to-protect-your-hair-from-sun-damage/>, published Aug. 22, 2014, p. 1-4.

Machine translation WO 2011/004133, printed 2017.

Wikipedia "Band Gap" last modified Jul. 18, 2017, https://en.wikipedia.org/wiki/Band_gap.

Machine translation WO 2012/046204, printed 2017.

Cuprous Oxide, Chemical Book, pp. 1-4, Accessed Sep. 18, 2017, https://www.chemicalbook.com/ProductChemicalPropertiesCB9853041_EN.htm.

Simon Aldridge and Anthony Downs. The Group 13 Metals Aluminum, Gallium, Indium and Thallium Chemical Patterns and Peculiarities, 2011 John Wiley & Sons, Ltd., p. 623 (Year: 2011).

English Language Translation of WO 2013 094639 (A1) (Year: 2013).

machine translation, JP 2008-024677, printer 2018.

Kelly et al. "The Optical Properties of Metal Nanoparticles: The Influence of Size, Shape and Dielectric Environment," Journal of Physical Chemistry B 107:668-677, 2003.

Garcia, "Surface Plasmons in Metallic Nanoparticles: Fundamentals and Applications," Journal of Physics D: Applied Physics 44(28), 283001, 2011.

\* cited by examiner

FIG. 1

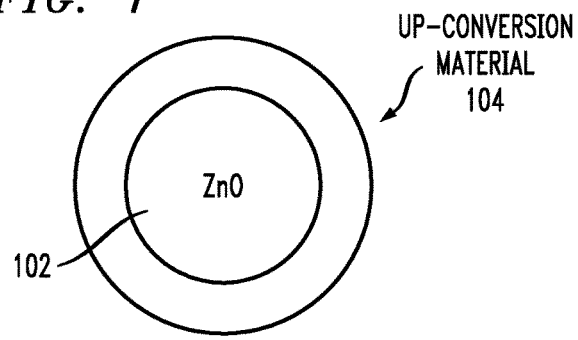

FIG. 2

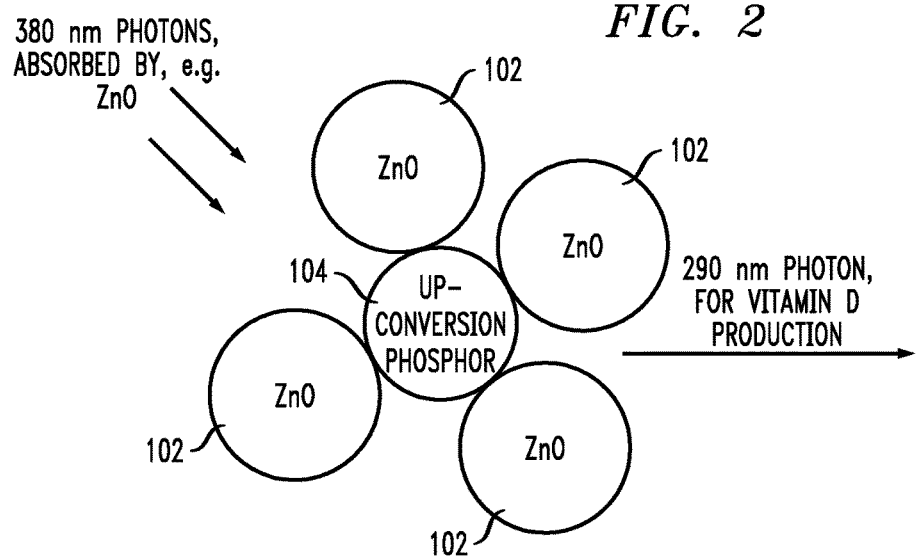

FIG. 3

302 — SELECT ONE OR MORE PHOSPHOR MATERIALS TO INCORPORATE INTO ONE OR MORE ZINC OXIDE PARTICLES IN A SUNSCREEN COMPOSITION, WHEREIN THE ONE OR MORE PHOSPHOR MATERIALS ARE CAPABLE OF CARRYING OUT AN UP-CONVERSION PROCESS WHEREBY TWO OR MORE PHOTONS ABSORBED BY (i) THE ONE OR MORE ZINC OXIDE PARTICLES AND/OR (ii) THE ONE OR MORE PHOSPHOR MATERIALS WITHIN A FIRST WAVELENGTH RANGE ARE EMITTED AS AT LEAST ONE PHOTON WITHIN A SECOND WAVELENGTH RANGE

304 — INCORPORATE THE ONE OR MORE SELECTED PHOSPHOR MATERIALS INTO THE ONE OR MORE ZINC OXIDE PARTICLES TO CREATE THE SUNSCREEN COMPOSITION

SUNSCREEN ADDITIVES FOR ENHANCING VITAMIN D PRODUCTION

CROSS-REFERENCE TO RELATED APPLICATIONS

The present application claims priority to United States Provisional Application Ser. No. 62/213,679, filed Sep. 3, 2015, incorporated by reference herein.

FIELD

The present application generally relates to chemical technology, and, more particularly, to sunscreen technologies.

BACKGROUND

Sunscreen creams and other such compositions are commonly used to prevent ultraviolet (UV) radiation (also referred to herein as "light" in this context) from reaching the skin of a human user and causing damage. It is noted that UV light is an electromagnetic radiation with a wavelength range between approximately 280 nanometers (nm) and approximately 400 nanometers (specifically, that is the range of UV radiation that is not absorbed by the ozone).

A common active ingredient of existing sunscreen compositions is zinc oxide (ZnO). ZnO is a semiconductor that has a specific band gap, and particles of ZnO used in existing sunscreen compositions are typically approximately 50-200 nm in size. Additionally, in existing sunscreen compositions, typical ZnO materials are capable of absorbing UV light (that is, blocking the UV light from passing through the sunscreen composition to be absorbed by the skin of the user) within a wavelength range of approximately 290 nm through only approximately 350-380 nm.

Additionally, high sun protection factor (SPF) sunscreen compositions, which can absorb a large majority of the UV light in the range of 290-380 nm, require the addition of a higher density of ZnO particles, which causes the composition to become white and/or opaque due to light scattering from the ZnO particles, and which is an often undesirable property to consumers.

Further, it is noted that some amount of high-energy light (for example, light within a wavelength range of approximately 270 nm to approximately 300 nm) is needed by the human body for producing vitamin D (which is useful, for example, in calcium absorption and bone growth). Accordingly, while existing sunscreen compositions are capable of blocking portions of UV light from passing through the composition to be absorbed by the skin of the user, such compositions simultaneously preclude the UV light responsible for aiding vitamin D production to be absorbed by the skin.

SUMMARY

In one embodiment of the present invention, sunscreen additives for enhancing vitamin D production and techniques related thereto are provided. An exemplary method can include selecting one or more phosphor materials to incorporate into one or more zinc oxide particles in a sunscreen composition, wherein the one or more phosphor materials are capable of carrying out an up-conversion process whereby two or more photons absorbed by (i) the one or more zinc oxide particles and/or (ii) the one or more phosphor materials within a first wavelength range are emitted as at least one photon within a second wavelength range. The method can also include incorporating the one or more selected phosphor materials into the one or more zinc oxide particles to create the sunscreen composition.

In another embodiment of the invention, a composition can include one or more zinc oxide particles suspended within a medium of a sunscreen composition, and one or more phosphor materials incorporated into the one or more zinc oxide particles, wherein the one or more phosphor materials are capable of carrying out an up-conversion process whereby two or more photons absorbed by (i) the one or more zinc oxide particles and/or (ii) the one or more phosphor materials within a first wavelength range are emitted as at least one photon within a second wavelength range.

These and other objects, features and advantages of the present invention will become apparent from the following detailed description of illustrative embodiments thereof, which is to be read in connection with the accompanying drawings.

BRIEF DESCRIPTION OF THE DRAWINGS

FIG. 1 is a diagram illustrating a ZnO particle configuration, according to an exemplary embodiment of the invention;

FIG. 2 is a diagram illustrating a configuration of ZnO particles, according to an exemplary embodiment of the invention; and FIG. 3 is a flow diagram illustrating techniques according to an embodiment of the invention.

DETAILED DESCRIPTION

As described herein, an embodiment of the present invention includes zinc oxide compositions, methods of fabrications thereof and methods of use thereof. Specifically, at least one embodiment of the invention includes providing sunscreen additives for enhancing vitamin D production.

As further detailed herein, one or more embodiments of the invention include generating ZnO compositions and methods of use thereof for effectively blocking more and/or all of the complete spectrum of UV light (that is, as noted above, the UV radiation that is not absorbed by the ozone, and which ranges between approximately 280 nm and 400 nm). Also, one or more embodiments of the invention include generating ZnO compositions and methods of use thereof for effectively modifying the band gap of a ZnO composition via the incorporation of one or more additional materials into the composition.

Further, as also detailed herein, one or more embodiments of the invention include generating ZnO compositions and methods of use thereof for permitting and/or accentuating a specific range (or "windows") of light (radiation) to pass through a ZnO composition such that the specific range of light can be absorbed by the skin of a human user. For example, at least one embodiment of the invention can include generating a ZnO composition that emphasizes reflection of light in a range of approximately 270-300 nm (which includes wavelengths that facilitate vitamin D absorption in the skin) to pass through the composition to be absorbed by the skin, while blocking harmful UV radiation at other wavelengths.

At least one embodiment of the invention includes introducing light-emitting particles that emit light at 270-300 nm into a sunscreen composition. Such introduction can be carried out, for example, via a coating of a ZnO particle (such as depicted in FIG. 1) and/or via an anchor particle used to cluster and/or group multiple ZnO particles (such as depicted in FIG. 2). Also, one or more embodiments of the invention can include blending phosphor particles with ZnO particles without physically aggregating the phosphor particles and the ZnO particles together. Additionally, the above-noted light-emitting particles can include phosphors that operate via an up-conversion process. As used herein, an "up-conversion" process includes converting two or more absorbed photons (with lower energy) into one emitted photon with higher energy (than the absorbed photons).

In one or more embodiments of the invention, an up-conversion process can be utilized wherein two photons absorbed by a ZnO particle are coupled into the phosphor to create one higher-energy photon. Also, in at least one embodiment of the invention, the emitting particles can include wide band gap phosphors, either with or without emission activators (which can also be referred to as stepping stones to move-up states within a band gap). As further illustrated in FIG. 1 and FIG. 2, such particles (phosphors) can be mixed into a sunscreen composition to increase the probability of vitamin D-producing light reaching the skin. Such a probability can be increased because the phosphors will emit and/or permit the passing of light at 276 nm, thereby resulting in additional light at 276 nm passing through to the skin. Accordingly, instead of blocking 100% of the vitamin D wavelength light (like ZnO does), at least some portion of such light can be transmitted.

FIG. 1 is a diagram illustrating a ZnO particle configuration, according to an exemplary embodiment of the invention. By way of illustration, FIG. 1 depicts a core-shell structure wherein a core of ZnO 102 is coated with a shell of an up-conversion material 104.

FIG. 2 is a diagram illustrating a configuration of ZnO particles, according to an exemplary embodiment of the invention. By way of illustration, FIG. 2 depicts an integration of an up-conversion phosphor particle 104 into a cluster of ZnO particles 102 within a sunscreen composition. In such a configuration, the up-conversion phosphor particle 104 can up-convert the light absorbed by the ZnO particles, or the up-conversion phosphor particle 104 can up-convert light it absorbs itself (through one or more emission activators, that is, the energetic steps inside of the band gap). As illustrated in FIG. 2, 380 nm photons can be absorbed by the ZnO particles 102, and the up-conversion phosphor particle 104 can up-convert those photons and emit a 290 nm photon (which is useful in vitamin D production).

In one or more embodiments of the invention (such as the example embodiments depicted in FIG. 1 and FIG. 2), one up-conversion phosphor particle or a combination of multiple distinct up-conversion phosphor particles can be utilized and/or integrated with one or more ZnO particles. Additionally, in one or more embodiments of the invention, such phosphor materials can include, for example, yttrium aluminum garnet (YAG) ($Y_3Al_5O_{12}$), and/or rare earth doped YAG, doped via dopants such as, for example, europium (Eu), dysprosium (Dy), cerium (Ce), samarium (Sm), and terbium (Tb). Also, phosphor materials can additionally include, for example, metal phosphates such as fluorapatite ($Ca_5(PO_4)_3F$), $LaPO_4:Ce^{3+}$, and $LaPO_4:Tb^{3+}$. Further, phosphor materials can also include, for example, rare earth borates such as lanthanum borate ($LaBO_3$) and yttrium borate ($YBO_3$), as well as doped versions of these materials.

Additionally, one or more embodiments of the invention can include utilizing quantum confinement. By way of illustration, in an example embodiment of the invention, an up-conversion phosphor particle, which conventionally emits light at wavelengths between 300-350 nm, can be manipulated to decrease the size of the particle, such that quantum confinement influences its electronic structure, in order to increase the band gap of the phosphor and to generate a blue shift emission of less than 350 nm.

FIG. 3 is a flow diagram illustrating techniques according to an embodiment of the present invention. Step 302 includes selecting one or more phosphor materials to incorporate into one or more zinc oxide particles in a sunscreen composition, wherein the one or more phosphor materials are capable of carrying out an up-conversion process whereby two or more photons absorbed by (i) the one or more zinc oxide particles and/or (ii) the one or more phosphor materials within a first wavelength range are emitted as at least one photon within a second wavelength range. In at least one embodiment of the invention, the first wavelength range can include wavelengths between approximately 350 nanometers and 400 nanometers, and the second wavelength range can include wavelengths between approximately 270 nanometers and 300 nanometers.

The phosphor materials can include yttrium aluminum garnet, yttrium aluminum garnet doped with one or more rare earth elements (such as, for example, europium, dysprosium, cerium, samarium, and/or terbium), one or more metal phosphates (such as, for example, fluorapatite, $LaPO_4:Ce^{3+}$, and/or $LaPO_4:Tb^{3+}$), and/or one or more rare earth borates (such as, for example, lanthanum borate and/or yttrium borate).

Step 304 includes incorporating the one or more selected phosphor materials into the one or more zinc oxide particles to create the sunscreen composition. Incorporating the selected phosphor materials into the zinc oxide particles can include applying the one or more selected phosphor materials as a coating to the surface of each of the one or more zinc oxide particles. Additionally, incorporating the selected phosphor materials into the zinc oxide particles can include grouping the one or more zinc oxide particles around the surface of one of the selected phosphor materials. Further, in one or more embodiments of the invention, particles of the phosphor can be incorporated into the standard ZnO formulation.

The techniques depicted in FIG. 3 can also include decreasing the particle size of the one or more phosphor materials to emit the at least one photon within a third wavelength range.

Also, an additional embodiment of the invention includes a composition that includes one or more zinc oxide particles suspended within a medium of a sunscreen composition, and one or more phosphor materials incorporated into the one or more zinc oxide particles, wherein the one or more phosphor materials are capable of carrying out an up-conversion process whereby two or more photons absorbed by (i) the one or more zinc oxide particles and/or (ii) the one or more phosphor materials within a first wavelength range are emitted as at least one photon within a second wavelength range.

The terminology used herein is for the purpose of describing particular embodiments only and is not intended to be limiting of the invention. As used herein, the singular forms "a," "an" and "the" are intended to include the plural foul's as well, unless the context clearly indicates otherwise. It will be further understood that the terms "comprises" and/or "comprising," when used in this specification, specify the presence of stated features, steps, operations, elements, and/or components, but do not preclude the presence or addition of another feature, step, operation, element, component, and/or group thereof.

At least one embodiment of the present invention may provide a beneficial effect such as, for example, incorporating one or more up-conversion particles into a sunscreen composition to increase the probability of vitamin D-producing light reaching the skin of a user.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A method, comprising:
    selecting one or more phosphor materials to incorporate into one or more zinc oxide particles in a sunscreen composition, wherein the one or more phosphor materials are capable of carrying out an up-conversion process;
    incorporating the one or more selected phosphor materials into the one or more zinc oxide particles to create the sunscreen composition; and
    enabling one or more iterations of the up-conversion process whereby (i) two or more photons within a wavelength range of between approximately 350 nanometers and 400 nanometers are absorbed by the one or more zinc oxide particles, (ii) the two or more photons absorbed by the one or more zinc oxide particles are up-converted by the one or more phosphor materials, resulting in at least one photon within a wavelength range of between approximately 270 nanometers and 300 nanometers, and (iii) the at least one photon within a wavelength range of between approximately 270 nanometers and 300 nanometers is emitted from the sunscreen composition to be absorbed by skin of a human user of the sunscreen composition.

2. The method of claim 1, wherein the one or more phosphor materials comprise at least yttrium aluminum garnet.

3. The method of claim 1, wherein the one or more phosphor materials comprise at least yttrium aluminum garnet doped with one or more rare earth elements.

4. The method of claim 3, wherein the one or more rare earth elements comprises one or more of europium, dysprosium, cerium, samarium, and terbium.

5. The method of claim 1, wherein the one or more phosphor materials comprise one or more metal phosphates.

6. The method of claim 5, wherein the one or more metal phosphates comprises one or more of fluorapatite, $LaPO_4:Ce^{3+}$, and $LaPO_4:Tb^{3+}$.

7. The method of claim 1, wherein the one or more phosphor materials comprises one or more rare earth borates.

8. The method of claim 7, wherein the one or more rare earth borates comprises one or more of lanthanum borate and yttrium borate.

9. The method of claim 1, further comprising:
    decreasing the particle size of the one or more phosphor materials to emit the at least one photon within a third wavelength range.

10. The method of claim 1, wherein said incorporating the one or more selected phosphor materials into the one or more zinc oxide particles comprises applying the one or more selected phosphor materials as a coating to the surface of each of the one or more zinc oxide particles.

11. The method of claim 1, wherein said incorporating the one or more selected phosphor materials into the one or more zinc oxide particles comprises grouping the one or more zinc oxide particles around the surface of one of the selected phosphor materials.

12. A composition comprising:
    one or more zinc oxide particles suspended within a medium of a sunscreen composition; and
    one or more phosphor materials incorporated into the one or more zinc oxide particles, wherein the one or more phosphor materials are capable of carrying out an up-conversion process whereby (i) two or more photons within a wavelength range of between approximately 350 nanometers and 400 nanometers are absorbed by the one or more zinc oxide particles, (ii) the two or more photons absorbed by the one or more zinc oxide particles are up-converted by the one or more phosphor materials, resulting in at least one photon within a wavelength range of between approximately 270 nanometers and 300 nanometers, and (iii) the at least one photon within a wavelength range of between approximately 270 nanometers and 300 nanometers is emitted from the sunscreen composition to be absorbed by skin of a human user of the sunscreen composition.

13. The composition of claim 12, wherein the one or more phosphor materials are applied as a coating to the surface of each of the one or more zinc oxide particles.

14. The composition of claim 12, wherein the one or more phosphor materials are incorporated into the one or more zinc oxide particles via grouping the one or more zinc oxide particles around the surface of one of the phosphor materials.

15. The composition of claim 12, wherein the one or more phosphor materials comprise at least yttrium aluminum garnet.

16. The composition of claim 12, wherein the one or more phosphor materials comprise at least yttrium aluminum garnet doped with one or more rare earth elements.

17. The composition of claim 16, wherein the one or more rare earth elements comprises one or more of europium, dysprosium, cerium, samarium, and terbium.

18. The composition of claim 12, wherein the one or more phosphor materials comprise one or more metal phosphates, wherein the one or more metal phosphates comprises one or more of fluorapatite, $LaPO_4:Ce^{3+}$, and $LaPO_4:Tb^{3+}$.

19. The composition of claim 12, wherein the one or more phosphor materials comprises one or more rare earth borates, wherein the one or more rare earth borates comprises one or more of lanthanum borate and yttrium borate.

* * * * *